United States Patent
Wolff et al.

(10) Patent No.: US 10,688,237 B2
(45) Date of Patent: Jun. 23, 2020

(54) APPARATUS AND METHOD FOR DETECTING VENOUS NEEDLE DISLODGEMENT

(71) Applicant: B. BRAUN AVITUM AG, Melsungen (DE)

(72) Inventors: Henrik Wolff, Witzenhausen (DE); Kai-Uwe Ritter, Rednitzhembach (DE)

(73) Assignee: B. BRAUN AVITUM AG, Melsungen (DE)

( * ) Notice: Subject to any disclaimer, the term of this patent is extended or adjusted under 35 U.S.C. 154(b) by 578 days.

(21) Appl. No.: 14/630,797

(22) Filed: Feb. 25, 2015

(65) Prior Publication Data
US 2015/0246171 A1 Sep. 3, 2015

(30) Foreign Application Priority Data
Feb. 28, 2014 (DE) .......................... 10 2014 102 731

(51) Int. Cl.
*A61M 1/36* (2006.01)
*A61M 1/14* (2006.01)

(52) U.S. Cl.
CPC ............ *A61M 1/3656* (2014.02); *A61M 1/14* (2013.01); *A61M 2205/13* (2013.01);
(Continued)

(58) Field of Classification Search
CPC .............. A61M 1/3639; A61M 1/3653; A61M 1/3656; A61M 1/10; A61M 1/1006; A61M 1/1086; A61M 1/14; A61M 1/3621
See application file for complete search history.

(56) References Cited

U.S. PATENT DOCUMENTS

| 4,501,583 A | * | 2/1985 | Troutner ............. A61M 1/3639 128/DIG. 13 |
| 5,711,883 A | * | 1/1998 | Folden .................... A61M 1/16 210/646 |

(Continued)

FOREIGN PATENT DOCUMENTS

| CN | 102105182 A | 6/2011 |
| CN | 204972388 U | 1/2016 |

(Continued)

OTHER PUBLICATIONS

European Search Report (with translation) for EP15154745.2 dated Jul. 14, 2015.
(Continued)

*Primary Examiner* — Scott J Medway (57) ABSTRACT

Apparatus that detect an interruption of the connection between a blood treatment apparatus and a patient blood circulation which can be connected to the blood treatment apparatus via a connection means is described. The connection means can be attached to a fluid line. The apparatus includes a line shut-off and a pressure sensor which is configured to measure the fluid pressure prevailing in the fluid line at a position located between the line shut-off and the connection means. A control and evaluation unit is configured to evaluate the pressure or pressure curve occurring after blocking the line so as to detect an interruption or disturbance of the connection between the connection means and the patient blood circulation.

17 Claims, 5 Drawing Sheets

(52) U.S. Cl.
CPC ..... *A61M 2205/14* (2013.01); *A61M 2205/15* (2013.01); *A61M 2205/17* (2013.01); *A61M 2205/18* (2013.01); *A61M 2205/3334* (2013.01); *A61M 2205/3344* (2013.01); *A61M 2205/583* (2013.01)

(56) References Cited

U.S. PATENT DOCUMENTS

| | | | |
|---|---|---|---|
| 6,090,048 A | 7/2000 | Hertz et al. | |
| 6,221,040 B1* | 4/2001 | Kleinekofort | A61M 1/16 604/4.01 |
| 6,595,942 B2 | 7/2003 | Kleinekofort | |
| 6,595,992 B1 | 7/2003 | Wagner et al. | |
| 6,623,443 B1* | 9/2003 | Polaschegg | A61M 1/3639 210/646 |
| 7,648,474 B2 | 1/2010 | Paolini et al. | |
| 2003/0009123 A1* | 1/2003 | Brugger | A61M 1/3626 604/4.01 |
| 2003/0128125 A1 | 7/2003 | Burbank et al. | |
| 2003/0194894 A1* | 10/2003 | Wariar | A61M 1/16 439/191 |
| 2003/0195454 A1* | 10/2003 | Wariar | A61M 1/3653 604/5.01 |
| 2005/0065459 A1* | 3/2005 | Zhang | A61M 1/342 604/4.01 |
| 2005/0131332 A1* | 6/2005 | Kelly | A61M 1/1696 604/4.01 |
| 2006/0081517 A1* | 4/2006 | Toyoda | A61M 1/3656 210/85 |
| 2007/0010779 A1* | 1/2007 | Utterberg | A61M 1/3653 604/4.01 |
| 2008/0065006 A1 | 3/2008 | Roger et al. | |
| 2010/0022934 A1 | 1/2010 | Hogard | |
| 2010/0089837 A1* | 4/2010 | Inoue | A61M 1/3656 210/741 |
| 2011/0028881 A1* | 2/2011 | Basaglia | A61M 1/14 604/4.01 |
| 2011/0034814 A1 | 2/2011 | Kopperschmidt | |
| 2011/0230772 A1 | 9/2011 | Koball et al. | |
| 2011/0301472 A1 | 12/2011 | Grober et al. | |
| 2012/0205312 A1 | 8/2012 | Hogard | |
| 2013/0204174 A1 | 8/2013 | Olde et al. | |
| 2015/0044099 A1* | 2/2015 | Yamanaka | A61M 1/367 422/82.08 |
| 2015/0246171 A1 | 9/2015 | Wolff et al. | |

FOREIGN PATENT DOCUMENTS

| | | |
|---|---|---|
| DE | 10 2008 015 832 | 10/2009 |
| DE | 10 2008 059 379 | 6/2010 |
| DE | 10 2008 061 122 | 6/2010 |
| EP | 1 584 339 | 10/2005 |
| EP | 2 218 470 | 8/2010 |
| EP | 2 318 073 | 5/2011 |
| WO | WO 97/10013 | 3/1997 |
| WO | WO 2011/080187 | 7/2011 |
| WO | WO 2012/175267 | 12/2012 |

OTHER PUBLICATIONS

German Search Report for DE 10 2014 102 731.0 dated Dec. 10, 2014.
German Search Report for DE 10 2014 102 732.9 dated Dec. 8, 2014.
Entire patent prosecution history of U.S. Appl. No. 14/627,330, filed, Feb. 20, 2015, entitled, "System and Method for Detecting Venous Needle Dislodgement.".
European Search Report dated Jul. 14, 2015 in European Application No. 15154745.2, including partial translation.
European Search Report for EP 15 15 4748 dated Jul. 3, 2015.
Office Action for U.S. Appl. No. 14/627,330 dated Jun. 17, 2016.
Chinese Office Action for Chinese Application No. 201510090181.6, dated Mar. 15, 2018, including English translation, 19 pages.

* cited by examiner

APPARATUS AND METHOD FOR DETECTING VENOUS NEEDLE DISLODGEMENT

CROSS REFERENCE TO RELATED APPLICATIONS

This application claims priority to German application DE 10 2014 102 731.0 filed Feb. 28, 2014, the contents of such application being incorporated by reference herein.

FIELD OF THE INVENTION

The invention relates to an apparatus and a method for detecting venous needle dislodgement as well as an apparatus for extracorporeal blood treatment equipped with the same. The apparatus for extracorporeal blood treatment can be configured for carrying out a blood treatment therapy such as hemodialysis, hemofiltration or hemodiafiltration. In this case preferably an apparatus for monitoring a vascular access during extracorporeal blood treatment is used.

BACKGROUND

For blood treatment the blood of a patient can be guided via an extracorporeal blood circulation, for example in the course of hemodialysis, hemofiltration or hemodiafiltration. In order to obtain access to the patient's vascular system arteriovenous fistulae, shunts or else vascular implantations can be used. The connection of the extracorporeal blood circulation to the patient is usually made via catheters or cannulas or, respectively, needles, e.g. dialysis cannulas or needles, by which a fistula or a shunt or, respectively, a vascular implantation, for example, is punctured and fluid communication is established in this way.

At the beginning of or else during blood treatment the case may occur that the venous access to the blood circulation is disturbed, if, for example, the needle or cannula gets out of place and the extracorporeal circulation is no longer connected properly, or is no longer connected at all, to the intracorporeal blood circulation, i.e. the patient's blood circulation. This may cause problems especially in the case of dislodgement of the venous access to the patient's blood circulation. Unless such dislodgement of the venous access is detected in due time, blood continues being withdrawn from the patient via the arterial access but is no longer properly returned into the patient's body after the extracorporeal blood treatment. In the case of common blood flow rates of 300 to 400 ml/min, for example, a critical situation will develop within a few minutes.

DESCRIPTION OF THE RELATED ART

EP 1 584 339 B1 discloses a method for detecting needle dislodgement based on the measurement of arterial and venous pressures while sums and differences are formed.

In an apparatus according to U.S. Pat. No. 7,648,474 B2 the arterial and venous pressure values are monitored for determining needle dislodgement.

SUMMARY OF THE INVENTION

Aspects of the invention provide an apparatus and a method.

By the apparatus according to aspects of the invention and the method according to aspects of the invention for example venous needle dislodgement can be detected at an early stage and in this way high patient safety during a treatment such as a dialysis treatment as well as high functional reliability of the apparatus according to aspects of the invention can be ensured.

Further developments of aspects of the invention are defined in the dependent claims.

Embodiments of the apparatus according to aspects of the invention serve for detecting an interruption of the connection between a blood treatment apparatus and a patient blood circulation which can be connected to the blood treatment apparatus via a connection means, for example a needle. The connection means, for example the needle, can be attached to a fluid line, optionally to the end thereof. One or more embodiments of the apparatus according to aspects of the invention include a line shut-off, a pressure sensor configured to measure the fluid pressure prevailing in the fluid line at a position located between the line shut-off and the connection means and a control and evaluation unit configured to evaluate the pressure or pressure curve occurring after blocking the line so as to detect herefrom an interruption or disturbance of the connection between the connection means and the patient blood circulation. An interruption or disturbance of the connection is also referred to as needle dislodgement in the foregoing and hereinafter.

The apparatus can be part of a blood treatment apparatus, for example a dialysis apparatus. A display and/or alarm device can be provided for generating a display or an alarm in the case of detection of an interruption or disturbance of the connection.

The apparatus may be configured to compare the pressure occurring in the fluid line and being measured continuously or repeatedly after closing the line shut-off to a threshold and/or to determine the rate of the pressure drop and/or to determine a final pressure value which tends to be resulting and/or to detect whether the pressure tends toward atmospheric pressure or a higher pressure occurring in the patient blood circulation.

The apparatus may include a blood pump which continues to be operable even after actuation of the line shut-off with corresponding fluid blocking of the fluid flow through the line shut-off, wherein the pumped fluid can be intermediately stored in a collecting means, for example a bubble collector.

The apparatus may be configured to stop the operation of the blood pump, when a collecting means receiving the pumped fluid is filled with the line shut-off being closed and/or when dislodgement of the connection means is determined and/or when a fluid pressure measured by the pressure sensor reaches or falls below a particular limit.

By aspects of the invention also a method for detecting an interruption of the connection between a blood treatment apparatus and a patient circulation is provided which can be connected to the blood treatment apparatus via a connection means, e.g. a needle. The connection means, e.g. the needle, can be attached to a fluid line, optionally to the end thereof. In one or more of the embodiments of the method the fluid pressure prevailing in the fluid line is measured via a pressure sensor at regular or irregular time intervals at a position located between a line shut-off and the connection means, wherein the fluid line is blocked at regular or irregular time intervals and the pressure or pressure curve occurring in the fluid line after blocking the fluid line is evaluated so as to detect herefrom an interruption or disturbance of the connection between the connection means and the patient blood circulation.

If an interruption of the connection is detected, a display or an alarm can be generated.

The pressure occurring in the fluid line and being measured continuously or repeatedly after closing the line shut-off can be compared to a threshold and/or the rate of the pressure drop can be determined and/or a final pressure value to be expected can be determined and/or it can be detected whether the pressure tends toward atmospheric pressure or a higher pressure occurring in the patient blood pressure.

A blood pump may continue to operate even after actuating the line shut-off with corresponding fluid blocking of the fluid flow through the line shut-off, wherein the pumped fluid is intermediately stored in a collecting means, for example a bubble collector.

The operation of a blood pump can be stopped, when a collecting container receiving the pumped fluid is filled with the line shut-off being closed and/or when dislodgement of the connection means is determined and/or when a fluid pressure measured by the pressure sensor reaches or falls below a particular limit.

The line shut-off can be re-opened as soon as it is detected that no interruption or disturbance of the connection is provided between the blood treatment apparatus and the connection means.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

It is possible by embodiments of the apparatus according to aspects of the invention and of the method according to aspects of the invention to detect venous needle dislodgements (VND), as they are called. For example, due to movements of the patient or insufficient fastening of the needle, the needle can get out of place or even completely slip out of the puncture site. This is problematic especially in the area of the venous needle, as the blood is returned to the patient via said needle, the blood being correspondingly pressurized in this case. This can even further increase the risk of undesired dislodgement up to slip-out of the needle.

In the present context, by the term needle dislodgement both complete slipping of the needle out of the venous vascular access and only partial dislodging of the needle with a restricted connection which is still existing to a certain extent, however, to the blood circulation is understood. When the needle gets out of place only partially, the needle can be located in the tissue surrounding the actual access site and cause perivascular hemorrhage there.

For detecting venous needle dislodgement in general the venous pressure can be monitored. However, mainly in the case of smaller cannula cross-sections the pressure drop at the cannula may be rather high so that no significant pressure drop is evident, even if venous needle dislodgement has taken place. Also hydrostatic pressure variations can impede or rule out the detection of pressure variations due to dislodgement.

In embodiments of the apparatus according to aspects of the invention and the method according to aspects of the invention it is provided to stop or at least restrict the fluid flow, i.e. the blood flow, before or during pressure measurement or pressure monitoring is carried out. In this way the afore-mentioned problem of high flow resistance in the cannula with the related offset in the measuring signal can at least be reduced.

Hereinafter blood guiding, e.g. a system or an arrangement in which fluid, e.g. blood, withdrawn from an object or a patient is guided outside the patient blood circulation in the extracorporeal circulation and is subsequently supplied to the patient blood circulation again, is referred to as extracorporeal circulation. The venous branch of the extracorporeal circulation may comprise, for example, a tube returning the fluid from the treatment apparatus to the object or patient, namely, discharging the fluid, which can also be in the form of a blood discharge line of the dialyser.

Embodiments of the invention do not only allow detecting an insufficient connection of a cannula such as a venous cannula up to the slip-out of the cannula from the access site provided, but also detecting a blood leakage in the venous branch downstream of the apparatus for detecting an interruption of connection. This may be realized, for example, in a double-needle operation of the blood treatment machine such as the dialysis machine.

Figure 1:
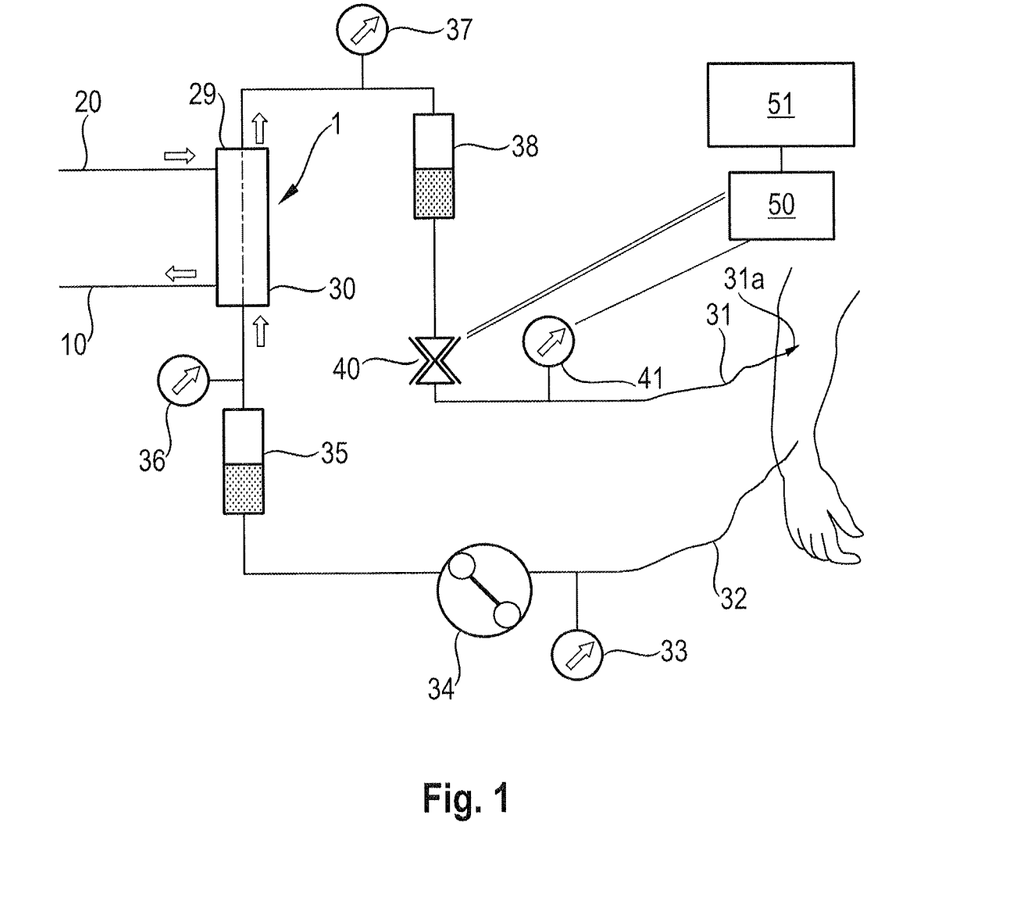
FIG. 1 shows an embodiment of an apparatus according to aspects of the invention.

FIG. 1 shows an embodiment of a dialysis apparatus according to aspects of the invention as well as an embodiment of an apparatus according to aspects of the invention for detecting venous needle dislodgement as well as a configuration of a method according to aspects of the invention for detecting such venous needle dislodgement in an embodiment of a dialysis method according to aspects of the invention.

FIG. 1 illustrates an embodiment of a dialysis apparatus equipped with an embodiment of a system for detecting venous needle dislodgement. The embodiment shown in FIG. 1 of the apparatus according to aspects of the invention for detecting a faulty or missing connection of a venous communication between the extracorporeal blood circulation and the patient blood circulation is illustrated by way of a dialysis machine. Instead of or in addition to hemodialysis also pure hemofiltration or hemodiafiltration can be realized.

The embodiment according to FIG. 1 comprises a dialyser 1 divided by a semipermeable membrane into a first chamber 29 arranged in a dialysis fluid path and a second chamber 30 which in turn is connected to the dialyser inlet with a blood supply line 32 leading away from the patient blood circulation. Via a dialysis outlet including a blood discharge line 31 leading to the patient the second chamber 30 is connectable to the blood circulation of the patient so as to supply the purified blood to the latter again. The first chamber 29 is connected to an intake 20 for fresh dialysis fluid and a drain 10 for used dialysis fluid.

Via a pressure sensor 41 the venous pressure can be detected after clamping off a tube shut-off (tube shut-off clamp or tube clamp) 40 and/or after stopping a blood pump 34. The tube clamp 40 can be operated manually or automatically and can cause complete or only partial shut-off of the fluid flow circuit back to the venous access of the patient. In the embodiment according to FIG. 1 the additional pressure sensor 41 for the venous pressure is disposed between the tube clamp 40 and the venous patient access and consequently is located in the blood return line to the patient. Since the pressure sensor 41 is arranged at the blood discharge line 31 directly ahead of the patient or in any case downstream of the tube clamp 40, the pressure from the patient access is adjusted at the pressure sensor 41 in the case of proper connection to the patient circulation, whereas the atmospheric pressure is measured, if the needle has slipped completely or partly out of the patient access.

The embodiment includes the pressure sensor 41 in the tube (blood discharge line) 31 supplying blood to a venous needle 31a, which tube is arranged downstream of the tube shut-off or tube clamp 40 and upstream of the needle 31a, i.e. at the line portion between the tube shut-off 40 and the needle 31a. As illustrated in FIG. 1, in the arterial branch 32 of the extracorporeal blood circulation, i.e. in the circulation leading from the patient to the dialyser inlet, there is arranged a pressure sensor 33 at the blood supply line 32 leading from the patient to the dialyser inlet and a bubble collector 35 between which the blood pump 34 is inserted in the blood supply line 32. Another pressure sensor 36 detects the pressure of the blood directly at the dialyser inlet of the dialyser 1. The dialysis fluid is guided in the direction symbolized by the arrows via the dialysis fluid supply line 20 to a first chamber 29 of the dialyser 1 and from there is guided via the dialysis fluid discharge line 10 to the drain or waste. The blood to be purified flows through the second chamber 30 of the dialyser 1 and is guided at the dialyser outlet in the arrow direction to the blood discharge line 31.

In the blood discharge line 31 another bubble collector 38 is optionally provided. A pressure sensor 37 detects the pressure in the blood discharge line 31 at the outlet of the dialyser 1.

The flow shut-off 40, which may also be in the form of a tube shut-off or a tube shut-off clamp, is provided, viewed in the blood flow direction, upstream of the pressure sensor 41 arranged at or in the blood discharge line 31. The blood supply line 32 and the blood discharge line 31 can be tubes, for example.

In the embodiment the blood of a patient is guided in an extracorporeal circulation and flows through the tube 32 into the blood-side chamber 30 of the dialyser 1, whereupon the purified blood is returned to the patient through the blood discharge line 31.

The flow rate of the blood circulation (extracorporeal) is controlled by the blood pump 34, wherein at or in the tube 32 the pressure sensor unit 33 for arterial pressure measurement is disposed upstream (viewed in the flow direction).

The bubble collector 35 serves for collecting the air bubbles in the arterial tube segment, wherein a further pressure sensor unit 36 is provided between the bubble collector 35 and the dialyser 1.

In the shown embodiment, the pressure sensor 41 is arranged between the tube shut-off 40 and the patient at or in the blood discharge line 31.

The dialysis fluid of the dialysis fluid chamber 29 of the dialyser is supplied via the dialysis fluid supply line 20, the dialysis fluid chamber 29 being separated from the blood chamber 30 by a semipermeable membrane. The dialysis fluid is provided by a fluid source (not shown), flows through the tube 20 and is pumped through a pump (not shown) into the chamber 29 of the dialyser, flows through the same and is subsequently supplied to a waste container via the tubing system 10.

In the blood supplying tube (blood supply line) 31 downstream of the dialyser 1 the pressure sensor 37 for venous pressure measurement is arranged followed by the bubble collector 38. In the flow direction the tube shut-off 40, for instance in the form of a tube shut-off clamp, follows hereto so as to disconnect the patient on the venous side, for example in the case of fault or for specifically carrying out detection of needle dislodgement.

If the blood pump 34 is not stopped during measurement for venous needle dislodgement, preferably in the line area between the blood pump 34 and the tube shut-off 40 optionally a reservoir for receiving the pumped blood is provided. The pumped blood can also be received, for example, by the bubble collectors 35 and/or 38.

After measurement for possible needle dislodgement the blood intermediately stored in the bubble collector 38 and/or 35 can be slowly returned to the patient again after opening the tube shut-off 40 so that the storage volume of the bubble collectors 38 and/or 35 is available again for receiving blood during a subsequent measurement.

In one or more embodiments a level regulation in the storage volumes of the bubble collectors 35 and/or 38 is provided in this respect so that the level of the fluid quantity stored in the bubble collectors 35 and/or 38 is regulated to a desired level when the tube shut-off 40 is opened.

A control means, e.g. in the form of a data processing and storage unit 50, controls all elements shown in FIG. 1 via appropriate interfaces, wherein FIG. 1 only illustrates the connection to the pressure sensor 41 and the tube shut-off 40. The data processing and storage unit 50 also collects information about other parameters of the dialysis apparatus, e.g. blood flow, dialysis fluid flow and/or treatment period. These parameters are processed along with the measured data. The data processing and storage unit 50 serves for processing the measured pressure values as well as for controlling the blood shut-off and the measuring times. Furthermore, an internal or external storage unit may be present for storing the measuring values as well as the control times.

The measuring values of the pressure sensors 33, 36, 37 and 41 are transmitted via data communications, which may be cable-bound and/or wireless, to the data processing and storage unit 50 which is in the form of a data processing and evaluation unit so as to identify venous needle dislodgements.

The embodiment of the dialysis machine according to aspects of the invention or the apparatus according to aspects of the invention for detecting needle dislodgement moreover includes an output unit 51 in the form of a warning signal unit or display which is connected to the data processing and storage unit 50 via a cable-bound or wireless data communication. The output unit 51 outputs an optical and/or acoustic warning signal and/or a text for explaining a problem on a display, for instance, if malfunction of the dialysis machine and/or the apparatus for detecting needle dislodgement and/or venous needle dislodgement is/are detected. Moreover, the output unit 51 can be configured for optical, acoustic or electronic output or an output in any other form, for example in the form of electronic storage, printout, e-mail transmission or the like.

The embodiment according to FIG. 1 may furthermore comprise additional measuring means, pumps, bubble collectors etc. which are not shown.

It may be provided in embodiments to simply stop or restrict the blood pump 34 so as to inhibit or to reduce the blood flow. Preferably alternatively or additionally, however, the tubing system guiding the purified blood to be supplied is also (completely or partly) disconnected ahead of the measuring device for the detection of, e.g. venous, needle dislodgement.

Figure 2:
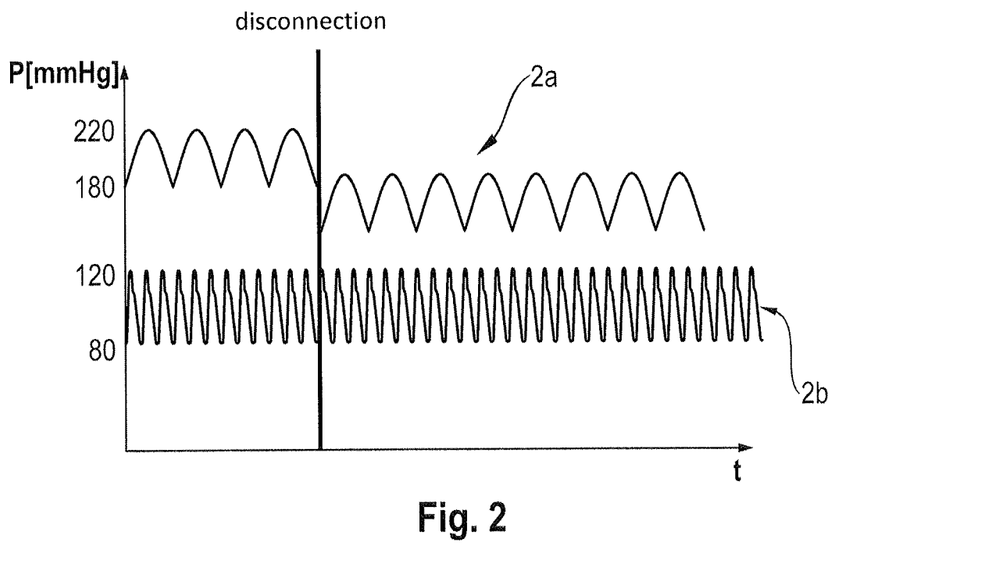
FIG. 2 shows a pressure curve before and after needle dislodgement.

FIG. 2 illustrates an example of a pressure curve at the pressure sensor 37 for venous pressure measurement before and after venous needle dislodgement, i.e. an undesired partial or complete separation of the connection between the dialysis apparatus and the patient blood circulation. The upper curve 2a symbolizes the venous pressure curve adjusted in the blood discharge line 31, while the lower steady curve 2b indicates the venous blood pressure in the access and thus in the body of the patient subjected to dialysis or to a blood treatment. The waveform of the upper pressure curve 2a is generated by the blood pump 34. The lower curve 2b constitutes the shunt or intravascular pressure and shows the pulsation modulated by the patient's heartbeat. The time of undesired needle dislodgement is shown by a vertical line. As is evident, after that the venous pressure curve decreases by about 20 to 40 mmHg. It is visible from FIG. 2 that the pressure drop after venous needle dislodgement at the pressure sensor 37 for venous pressure measurement is relatively small and merely amounts to about 20 to 40 mmHg. The pressure drop thus is within an order of magnitude which can also be caused by other reasons such as movements of the patient or lowering of the patient's table. Thus this decrease is rather difficult to detect in a reliable manner.

In embodiments of the invention the distinction of the reason for the change of pressure is considerably simplified, as the pressure pulses generated by the extracorporeal blood pump 34 are no longer included in the measuring signal, when the extracorporeal blood pump 34 is switched off or at least the blood flow is inhibited or at least restricted. Otherwise the pressure pulses are equally within the order of the pressure changes.

By embodiments of the apparatus according to aspects of the invention, which can also be referred to as system according to aspects of the invention, venous needle dislodgements can be detected easily, reliably and quickly.

In the embodiment of the apparatus according to aspects of the invention in accordance with FIG. 1, the air bubble collector 35 and/or 38 moreover serve as storage volumes, where appropriate, so that the blood pump 34 can continue running even when the clamp 40 is closed. Alternatively or additionally the blood pump 34 can also be switched off or continued to be operated to a reduced degree as regards its pumping rate when the clamp 40 is closed. In the embodiment the pressure is measured by the pressure sensor 41 with a stopped blood flow or with a blood flow at least reduced in a defined manner. In this embodiment of the apparatus according to aspects of the invention, the blood pump 34 can continue pumping even during and after closing the clamp 40 for detecting needle dislodgement and the course of the treatment is not impaired by the measurement at least on the arterial side.

The extracorporeal blood circulation can be monitored for detecting venous needle dislodgement in blood treatment apparatuses working in single-needle operation as well as in blood treatment apparatuses working in dual-needle operation including an arterial cannula and a venous cannula for producing the patient's access.

Thus the invention provides an apparatus and a method for detecting needle dislodgement at the vascular access, e.g. the venous vascular access. This apparatus and this method can be used, for instance, in an apparatus and a method for extracorporeal blood treatment, especially a chronical blood purification therapy such as hemodialysis, hemofiltration and hemodiafiltration. Thus the vascular access can be monitored during the extracorporeal blood treatment and both needle dislodgement and needle displacement at the venous vascular access can be safely identified. Even a blood leakage, e.g. in the venous branch, in the flow direction behind the clamp 40, of the extracorporeal circulation can be reliably detected.

The return of the purified blood leaving the dialyser 1 to the patient can be blocked or at least restricted by the tube shut-off 40.

Viewed in the direction of blood flow, in an embodiment the tube shut-off 40 may form the last but one component and the pressure sensor 41 may constitute the last component of the apparatus for extracorporeal blood treatment. The tube shut-off 40 the flow from the pressure sensor 41 to the return into the patient to be stopped or at least restricted by actuating the tube shut-off 40.

The pressure sensor 41 need not necessarily be the last component before the return of the blood to the patient. It is preferred, however, that between the pressure sensor 41 and the inlet site of the purified blood into the patient circulation no further components are provided which definitely influence the time progression of the pressure measured by the pressure sensor 41 during measurement, when the tube shut-off 40, e.g. tube shut-off clamp, is closed, in a significant or non-predictable manner. In one, more or all embodiments the tube shut-off 40 is provided ahead of the pressure sensor 41, viewed in the direction of blood flow. In one, more or all embodiments, viewed in the direction of blood flow, initially all other components, especially those which are capable of influencing the pressure such as bubble collectors, pressure sensors, measuring means etc. are provided starting from the dialyser 1 along the blood discharge line 31, wherein the tube shut-off 40 is positioned as the last but one of these components and the pressure sensor 41 is arranged in these or other embodiments as the last component of the embodiment of the apparatus of the invention, which is only followed, viewed in the direction of blood flow, by the needle leading into the patient the proper positioning and fluid connection of which is to be detected (dislodgement).

The tube shut-off 40 and the pressure sensor 41 are connected to the control means 50 which transmits instructions for blocking and releasing the fluid flow to the tube shut-off 40 and measures the pressure measured by the pressure sensor 41 after shut-off and herefrom detects whether or not a proper connection is provided between a dialysis system, especially a needle of the dialysis system, and the patient blood circulation.

Another embodiment of the invention provides an apparatus for extracorporeal blood treatment comprising a dialyser 1, a tube shut-off 40, a pressure sensor 41, a data processing unit, a storage unit, which may be part of the data processing unit, and an output unit. The dialyser 1 can be divided into first and second chambers 29, 30 by a semipermeable membrane, the first chamber 29 being arranged in a dialysis fluid path and the second chamber 30 being connectable to the blood circulation of a patient with a blood supply line 32 and a blood discharge line 31 of the dialyser 1. Furthermore, a bubble collector 35, 38 may be provided. The tube shut-off 40 and the pressure sensor 41 are preferably arranged in the blood discharge line 31 of the dialyser 1 behind, i.e. downstream of, the bubble collector 38.

The embodiment illustrated in FIG. 1 constitutes a possible structure of an apparatus according to aspects of the invention for extracorporeal blood treatment and/or for the detection of needle dislodgement. In another embodiment the pressure sensor 37 can be dispensed with, for example, as the function thereof can be assumed by the pressure sensor 41 provided in this embodiment and arranged according to the representation in FIG. 1.

By way of the measuring data sensed by the pressure sensor 41 in the embodiment according to FIG. 1 a regular examination for venous needle dislodgement is carried out. The regular examination can be a single check or a multi-check. A multi-check consists of at least two single examinations. Likewise threefold, fourfold to n-fold examinations can be carried out during dialysis, n being a natural number larger than or equal to 5.

The examination for venous needle dislodgement is implemented in that the tube shut-off 40 is closed so that no more blood can flow into the blood discharge line 31 through which the blood is returned to the patient again. Any apparatuses which inhibit the flow through the blood discharge line 31 in the form of a tube such as tube shut-off clamps or valves, can serve as tube shut-off 40.

When the tube 31 is disconnected, pressure measurement is then carried out at the pressure sensor 41 continuously or at, preferably regular, time intervals until it can be determined by way of the measured pressure values whether they tend toward atmospheric pressure.

Atmospheric pressure in this case means that the pressure toward which the pressure curve tends after closing the tube shut-off, does no longer include or reproduce the shunt or intravascular pressure, but that the system is open toward atmosphere via the needle connecting the blood discharge line 31 to the patient. In this case the pressure is no longer due to the counter-pressure in the patient access. A fluid loss occurs via the needle until the pressure inside the tubing system corresponds to the ambient pressure of the needle which is either the atmospheric pressure or the pressure in the venous patient access, each taking the hydrostatic pressure by a possible difference in height between the fluid level in the air bubble collector 38 and the venous access into account.

The reaching of the different pressure levels which depends on the pressure (atmospheric pressure or patient intravascular pressure) prevailing at the outlet of the needle leading to the patient access is also reflected by the speed at which the change of pressure takes place after stopping the flow by blocking the tube shut-off 40 in the measuring device. Here the duration of the drop of pressure e.g. to 36.8% of the value (1/e of the value) present with running blood flow, i.e. opened tube shut-off 40, can be used as a measure.

In addition or as an alternative, it can optionally be checked whether after closing the tube shut-off 40 a periodic signal can be proven which is superimposed to the pressure signal and is generated by the pulsating blood pressure in the patient access. If such pulsating periodic signal cannot be proven any more, this is equally indicative of venous needle dislodgement, as no connection to the patient circulation system is provided any more. If needle dislodgement is detected, preferably a warning signal is output. In one or more embodiments the tube shut-off 40 in such case remains closed so that undesired discharge of the blood into the needle exposed to the atmosphere or undesirably leading into the patient tissue is prevented. During the examination for venous needle dislodgement the tube shut-off 40 remains closed.

If it is detected when checking for needle dislodgement that no needle dislodgement is provided, i.e. the dialysis machine is correctly connected to the blood circulation of the patient, the tube shut-off 40 is re-opened and the dialysis is continued until a repeated check for venous needle dislodgement is carried out after a predetermined time interval. The intervals between the checks for venous needle dislodgement can be automatically determined or adjustable, e.g. for high-risk patients tending to uncontrolled movements. In embodiments of the apparatus according to aspects of the invention the time interval between the checks lies within the range of from 2 seconds to 5 minutes or within the range of from 10 seconds to 4 minutes or within the range of from 20 seconds to 3 minutes or within the range of from 25 seconds to 120 seconds, or else within the range between 30 and 60 seconds so that a check is carried out once or twice a minute.

In one or more embodiments, the time intervals between the checks can be determined automatically depending on the patient's weight and the blood flow adjusted. About 13% of the total blood volume of the patient can be withdrawn, before an effect on the arterial pressure of the patient or on his/her cardiac output will occur. For example, in one embodiment with the knowledge of the blood volume of the patient of e.g. 6 liters and a blood flow rate of 300 ml/min the scanning frequency can be determined to be 0.0083 Hz, i.e. to a measurement every 2 minutes. The loss of blood becomes critical when 35 to 45% of the blood volume is withdrawn. Herefrom an absolute minimum value for the scanning frequency can be determined. Further dependent parameters can be the heart and/or respiratory rate, accompanying diseases such as Diabetes mellitus and/or coronary heart diseases. An adjustable individual check can be manually carried out or automatically triggered e.g. after an unusual unspecific pressure drop at the pressure sensor 37. If, for example, a pressure drop of more than a reference value of e.g. 10% to 30% or more than the average pressure sensed by the pressure sensor 37 is determined at the pressure sensor 37, the individual check is triggered.

In embodiments of the apparatus according to aspects of the invention, as a further trigger criterion for the start of a new or additional measurement the detection of a strong drop of the venous pressure between the measuring intervals during a current treatment can be used. This means that with continuous pressure measurement at the pressure sensor 41, when the tube shut-off 40 is opened, automatically a new measurement is started, when major pressure variations or a pressure drop of e.g. more than 20% of the previously prevailing average pressure are detected during this continuous pressure measurement at the pressure sensor 41. The start of a new measurement means in this case, too, that the tube shut-off 40 is closed and it is measured at the pressure sensor 31 whether the pressure tends toward the atmospheric pressure.

Hereinafter the operating mode of the illustrated and described embodiment as well as a configuration of a method according to aspects of the invention for checking and/or detecting the presence of venous needle dislodgement will be described. By "venous needle dislodgement" also in this case a displacement including slipping out of the needle leading from the blood discharge line 31 into the patient and/or inadvertent separation or opening of the connection of the blood discharge line 31 to the patient access, for example in the form of a bayonet lock, twist lock or plug-in lock, are to be understood. For carrying out the check for venous needle dislodgement initially the tube shut-off 40, for example in the form of a tube shut-off clamp, is closed. As an alternative or in addition, the blood pump 34 can be stopped.

The pressure drop occurring at the pressure sensor 41 after closing the tube shut-off 40 is taken up at a sufficient dissolution and/or scanning rate, wherein the measuring values of the pressure drop or the respectively measured pressure established in this way are stored in the evaluation and storage unit 50. The storage unit can be an internal memory, for instance random access memory, or else an external memory. In one or more embodiments the dissolution rate referred to as scanning rate here is within the range of from 1 to 2000 measurements per second or within the range of from 2 to 1000 measurements per second or within the range of from 3 to 500 measurements per second or within the range of from 4 to 200 measurements per second or within the range of from 5 to 100 measurements per second or within the range of from 6 to 50 measurements per second. This ensures that the pressure curve is depicted at a quality and precision sufficient for analysis.

FIG. 2 illustrates an example of the pressure curve at the pressure sensor 41 before and after needle dislodgement. The pressure at the pressure sensor 41, i.e. the pressure measured by the same, is adjusted to the level of the vascular pressure at the patient access, i.e. in the shunt, for example. Here a pressure of 25 mmHg corresponds to the average internal shunt pressure of an AV shunt (arteriovenous shunt) consisting of autologous material. The average internal shunt pressure of all dialysis patients with native AV shunt and AV shunts with PTFE prosthesis amounts to about 35 mmHg. A value of about 40 mmHg corresponds to the average of 80% of all dialysis patients with native AV shunt. On average the internal shunt pressures of 80% of all dialysis patients with PTFE prosthesis are below 70 mmHg.

Hereinafter a pressure of 30 mmHg will be assumed by way of example. This is thus within the order of the typical pressure pulses generated by the blood pump 34 in the current therapy.

Figure 3:
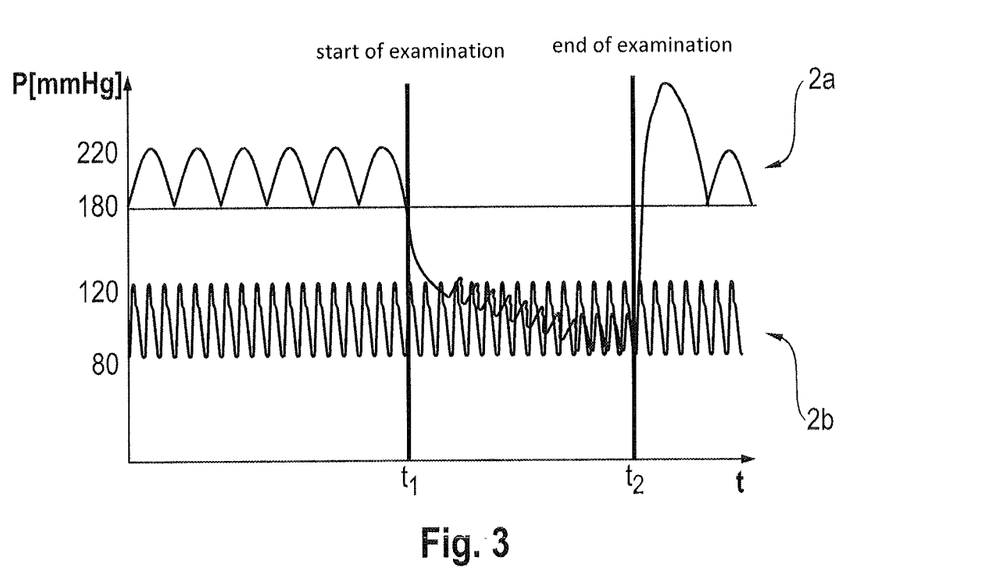
FIG. 3 shows an embodiment of a method for detecting needle dislodgement.

In the embodiment according to FIG. 3 possible venous needle dislodgement is detected when the blood flow is stopped. This can be done by stopping a blood pump 34 arranged in the arterial part of the extracorporeal circulation or else by disconnecting the tubing system with the tube clamp 40, while the blood pump 34 is running. In another embodiment both the blood pump 34 and the tube clamp 40 can be jointly controlled so that both the active fluid delivery through the blood pump 34 and the transmission of the blood through the tube clamp 40 are stopped simultaneously or else staggered in time. When the blood flow is stopped, the pressure in the entire extracorporeal blood tubing system runs against the shunt or intravascular pressure of the patient. FIG. 3 shows a typical curve progression for the pressure occurring at the pressure sensor 41 and measured by the same without venous needle dislodgement, wherein the measurement is started at a time $t_1$ and is stopped again at a time $t_2$.

Figure 4:
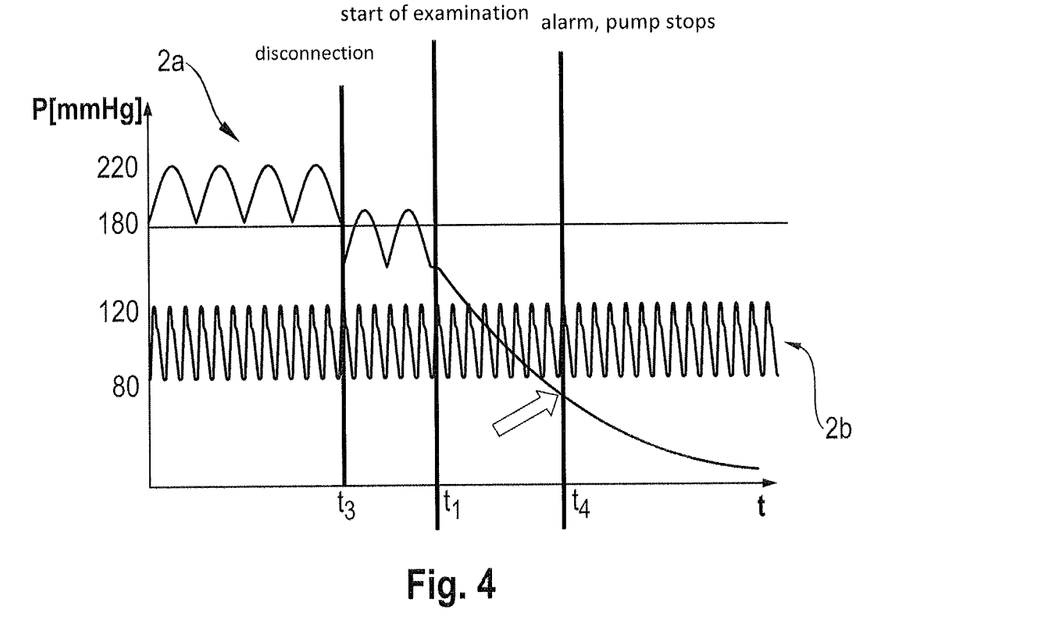
FIG. 4 shows a diagram of the pressure curve in time in the case of needle dislodgement and a subsequent check of dislodgement.

In the embodiment according to FIG. 4 undesired needle dislodgement or separation of the connection between the extracorporeal circulation and the patient access occurs at a time $t_3$. This needle dislodgement or separation of the connection to the patient access is detected during regular examination started at the time $t_1$ and after decrease of the measured blood pressure below a threshold $p_{Grenz}$ D at the time $t_4$ results in triggering an alarm and, if necessary, additionally in stopping the blood pump 34, if the latter is still running. The threshold $p_{Grenz}$ can be established, for example, in that an examination is carried out with a safely applied venous access. When the threshold $P_{Grenz}$ is underrun, additionally or alternatively to triggering a warning signal the dialysis process is interrupted and the apparatus for extracorporeal fluid treatment is transferred into a safe state without further withdrawal of fluid so that no damage is inflicted on the patient.

Venous needle dislodgement is detected in that pressure measuring values are measured at the pressure sensor 41 from the start of examination at the time $t_1$ staggered in time, i.e. at time intervals, and it is checked whether these pressure measuring values in their drop tend toward atmospheric pressure and reach and underrun, for example, the threshold $p_{Grenz}$. If the pressure measuring values measured at the pressure sensor 41 show a tendency toward atmospheric pressure, i.e. a relatively fast decrease or reaching and underrunning of the threshold $p_{Grenz}$, the presence of venous needle dislodgement and, respectively, an undesirably faulty connection between the blood discharge tube 31 and the patient access, e.g. the shunt, is concluded. If, however, the pressure measuring values measured at the pressure sensor 41 tend toward a typical venous pressure level and accordingly show only a small decrease rate and, respectively, do not reach or fall below the threshold $p_{Grenz}$, no venous needle dislodgement is given, and the examination is terminated at the time $t_2$ (FIG. 3) and the treatment, i.e. the dialysis, is continued. This case is illustrated in FIG. 3.

Hence, with the blood pump 34 running and the tube shut-off 40 being opened, for example, a pressure of 160 mmHg can be measured at the pressure sensor 41. If the subsequent pressure measurements at the pressure sensor 41 show a pressure drop tending toward atmospheric pressure, i.e. to a value of 0 mmHg relative to the atmospheric pressure, when the tube shut-off 40 is closed, venous needle dislodgement is present and a warning is output, for example in optical form as a visual display or in acoustic form by generating an acoustic alarm, and the blood pump 34 is stopped, where necessary, unless this has been done yet. If, however, the values of the pressure sensor determined at the pressure sensor 41 after the start of measurement tend e.g. toward 30 mmHg, this tendency value is within the range of a typical venous pressure level so that it is decided that no venous needle dislodgement is present.

In one or more embodiments of the invention, a prediction of the curve progression after closing the tube shut-off 40, e.g. the tube shut-off clamp, is provided so as to reduce the duration of the examination. This can be done in the embodiment(s) in that by way of the first measuring values after the start of examination at the time $t_1$ a value toward which the pressure curve tends is extrapolated. By way of the extent of pressure drop after closing the tube shut-off 40 a relatively reliable prediction can be made as to whether the pressure drop gradient tends toward the venous blood pressure of the patient or toward atmospheric pressure.

Instead of or in addition to the analysis of the pressure at the pressure sensor 41 with closed tube shut-off 40, also the course of the pressure drop can be used for detecting venous needle dislodgement. In an embodiment, e.g. the duration $\tau$ of the dying of the pressure to no more than 36.8%, i.e. to $1/e$, is used as parameter. This parameter differs significantly for the cases of connection and, respectively, dislodgement (FIG. 8) so that also herefrom a possible needle dislodgement can be reliably detected. The control unit 50 in this case checks the duration $\tau$ required to reach a pressure drop to $1/e$ or another specified value and compares this duration τ to a time threshold or reference value, where necessary. If the measured duration τ is below the time threshold, dislodgement is concluded. Otherwise the case of proper connection is concluded and the treatment is continued. This approach, too, constitutes a suitable means for detecting venous needle dislodgement.

In the afore-described or other embodiments it can be alternatively or additionally checked whether after closing the tube shut-off 40 a periodic signal continues to be measured at the pressure sensor 41. If so, no dislodgement is present as the periodic signal is generated by the pulsatile blood pressure. In this case the measurement can be directly interrupted and the dialysis can be continued. This course of action excels by the fact that the interruption of dialysis is extremely short. If, on the other hand, a drop of the pressure curve is obtained without any modulated periodic signal, dislodgement is possible or probable. In this case the measurement is continued in the described embodiment until an unambiguous result is obtained. In some cases or in several embodiments it may also be provided to completely stop the blood pump 34, for example when the extracorporeal storage volume provided by the bubble collector(s) 35, 38 or other components is exhausted. In all these cases the patient's safety is guaranteed.

Alternatively or additionally, during the examination for venous needle dislodgement the blood pump 34 can continue pumping. This leads to a variation of the fill level in the venous bubble collector 38 and/or in the arterial bubble collector 35 in which the quantity of the blood pumped in this period is intermediately stored. FIG. 3 illustrates that the pressure is measured in the venous tube (line) 31 returning the patient blood again after opening the tube shut-off 40, which results in an increase in pressure at the pressure sensor 41. Subsequent hereto the pressure falls to the basic level again, but not deeper than that. This course of action entails the advantage that no dialysis time is spoiled on checking for venous needle dislodgement, as the dialysis can be continued during this measuring period.

For determining the final point of pressure measurement at the pressure sensor 41 a fit or a threshold or desired curve progression can be employed. The assumed progression preferably is an exponential drop of the pressure according to the following formula:

$$F(t) = e^{(-at)} + A$$

wherein A is an offset value, i.e. the value toward which the function is converging, whereas a denotes the dying constant. This is only one of plural possible embodiments of the conversion. The behavior and/or the variables used for the comparison can also be described by exponential functions and polynomials.

The fit or, respectively, the threshold or, respectively, the reference curve can be dynamically adapted in the course of measurement and, respectively, during the measuring period. In this embodiment new data points, namely, new currently established measuring values, are immediately integrated in the fit, i.e. the desired curve or the threshold is adapted so as to render the prediction of the final value to be expected as precise as possible. Introducing additional information in the form of new values can also influence the calculated final value of the fit function or reference function, respectively. Consequently, the latter is exposed to a certain variation in this course of action. This variation can be used as additional control parameter for the reliability of the prediction of the final value. The smaller the variation, the more reliable and thus the more precise is the statement. If the established variation is within an interval of less than 20 mmHg, preferably less than 10 mmHg, or less than 5 mmHg, the measurement is judged to be completed.

By the final point of pressure measurement in this context the pressure value is understood which the pressure measured by the pressure sensor 41 would reach according to the prediction of the fit after closing the tube shut-off 40.

The afore-described embodiments of the apparatus according to aspects of the invention and the method according to aspects of the invention for examination for venous needle dislodgement excel by the fact that the venous pressure is uncoupled from the arterial pressure in the extracorporeal circulation and there is not simply determined the difference in pressure between the venous and arterial pressures. The arterial pressure curve therefore is no disturbing variable, and movements of the patient or an adjustment of the patient's lying height or lying position do not result in a false alarm. This is due to the fact that in embodiments of the apparatus according to aspects of the invention and the method according to aspects of the invention exclusively a pressure drop is measured in the venous pressure behind, or downstream of, a tube shut-off and it is observed whether the pressure drop tends toward atmospheric pressure or a pressure level common in the venous range. Thus a faultless and precise diagnosis can be made.

Hereinafter a concrete embodiment will be described. At the beginning of dialysis, first a pressure value is recorded as reference value by the pressure sensor 41 when the flow is interrupted (closing of the tube shut-off 40) and while a properly applied venous patient access is ensured. The exemplified value in this case is 35 mmHg. During the first treatment phase of the first two hours of treatment, for example, the tube shut-off 40 is now closed at intervals of e.g. 2 minutes and the pressure curve is recorded at the pressure sensor 41. An extrapolation of the pressure curve recorded over a particular period of e.g. 1.5 s carried out in the embodiment results in the fact that the counter-pressure at the venous needle ranges between e.g. 30 mmHg and 40 mmHg depending on the measurement. Thus the tube shut-off 40 can be immediately re-opened so as to regularly continue the treatment of the patient. After each measurement the intermediately stored blood volume accumulated in the air bubble collector 38 by the running blood pump 34 with the tube shut-off 40 being closed is gradually returned into the patient again. In order to avoid pressure peaks by opening the tube shut-off 40 the pressure can be balanced in the air bubble collectors 38 and 35. For this purpose, a pump is suited, for example, which is used for adjusting the fluid levels in the air bubble collectors 35, 38.

Also during this afore-described operation the blood pump 34 continues running at the delivery rate selected by the user of e.g. 300 ml/min so that, considered throughout the complete treatment, the average blood flow corresponds to the blood pressure selected by the user.

When the treatment is continued after measurement, i.e. in the described example in the third hour of treatment, venous needle dislodgement now occurs. In the subsequent measurement with closed tube shut-off 40 a pressure curve which tends toward atmospheric pressure (0 mmHg difference pressure) is detected at the pressure sensor 41. The venous needle remains on the patient's table, for example, and is provided level with the pressure sensor 41. As soon as this is detected, immediately alarm is triggered and the blood treatment is interrupted, if necessary, by stopping the blood pump 34. The nursing staff now can attend to the patient and remedy the situation. After that the treatment can be continued.

After a particular period of e.g. 40 minutes a pressure of −70 mmHg is measured, for instance, whereupon the blood pump 34 is stopped and alarm is triggered. In this example, the needle has not remained on the couch but has fallen to the ground. Thus the needle in this example is provided below the pressure sensor 41. The hydrostatic column between the pressure sensor 41 and the opening toward atmosphere (venous needle on the ground) thus generates negative pressure in the pressure sensor 41.

After a further period of e.g. 20 minutes in a subsequent measurement during extrapolation of the pressure curve from the measurement lasting e.g. 1.5 seconds, no unambiguous result is established. Simultaneously with the measurement, the patient has varied e.g. the position of his/her arm and thus caused a strong variation in the extrapolation of the pressure curve. At first the measurement is repeated after a specific period of 15 seconds, for example, so as to check the result of the previous measurement. Since in this example again no unambiguous statement can be made on the basis of the measuring results after e.g. 1.5 seconds, the tube shut-off 40 remains closed until an unambiguous result is provided. In such case, in addition to the bubble collector 38 initially used for intermediate storage of the purified blood also the bubble collector 35 can be used as blood reservoir for still unpurified blood, wherein in this case the delivery volume of the dialyser 1 can be restricted or completely reduced to zero. Hence the blood volume delivered while the blood pump 34 continues running is now intermediately stored in the bubble collector 35. If the result still is not sufficiently precise, the blood pump 34 in this case is equally stopped until an unambiguous result is achieved. In the described example, however, it is clear after a measuring time of e.g. 6 seconds that no venous needle dislodgement is present, as the extrapolated value now is 35 mmHg, i.e. the value which was recorded and stored as reference value for a proper access also at the beginning of the treatment. Hence the treatment is continued.

As afore-described, FIG. 3 shows a schematic pressure curve at the pressure sensor 41 with a correctly positioned venous needle 31a. The upper curve 2a also in this case symbolizes the venous pressure curve, while the lower steady curve 2b indicates the venous blood pressure in the body of the patient to be subjected to the blood treatment. At a "start of examination" time $t_1$ the tube shut-off 40 is closed and the pressure sensor 41 measures whether a periodic signal generated by the pulsating blood pressure of the patient continues being provided and/or whether the pressure measuring values measured by the pressure sensor 41 tend toward zero.

From the curve shown in FIG. 3 it is evident that the pressure drop does not tend toward zero but toward approximately 80 mmHg and further a periodic signal is continuously provided by the pulsatile blood pressure. It is detected herefrom that no needle dislodgement is present, and the blood treatment is continued after the end of examination at the time $t_2$. Accordingly, the tube shut-off 40 is re-opened, wherein a pressure maximum (overshooting) may occur due to the pressure built up ahead of (upstream of) the tube shut-off 40, as it is evident in the pressure curve progression 2a immediately after the time $t_2$.

FIG. 4 illustrates an example of a pressure curve at the pressure sensor 41 of the apparatus according to aspects of the invention and the method according to aspects of the invention in the case of venous needle dislodgement. The upper curve 2a also in this case symbolizes the venous pressure curve, whereas the lower curve 2b indicates the venous blood pressure in the body of the patient to be dialyzed. In the example according to FIG. 4, at the time $t_3$ needle dislodgement, i.e. separation of the connection between the blood treatment apparatus and the patient blood circulation, has occurred for example by slip-out of the venous needle or by separation of the fluid communication established in any way between the dialysis apparatus and the patient blood circulation. The tube shut-off 40 is closed at the time $t_1$ "start of examination". Two pump strokes before the time $t_1$, i.e. the start of examination, at the time $t_3$ in fact needle dislodgement did occur. Now the pressure in the blood discharge line 31 tends toward atmospheric pressure after closing the tube shut-off 40 so that also the pressure measured at the pressure sensor 41 tends toward atmospheric pressure. The detection of this curve progression by the pressure measurements at the pressure sensor 41 permits the unambiguous statement that venous needle dislodgement is present. For this purpose, the omission of the venous pulsations in the measured pressure signal just as the gradient of drop of the measured pressure and/or the falling of the measured pressure below a threshold can be evaluated and detected at a time $t_4$. If venous needle dislodgement is determined, an optical, visual or other alarm can be generated at the time $t_4$ and from this time also the blood pump 34 can be stopped.

Figure 5:
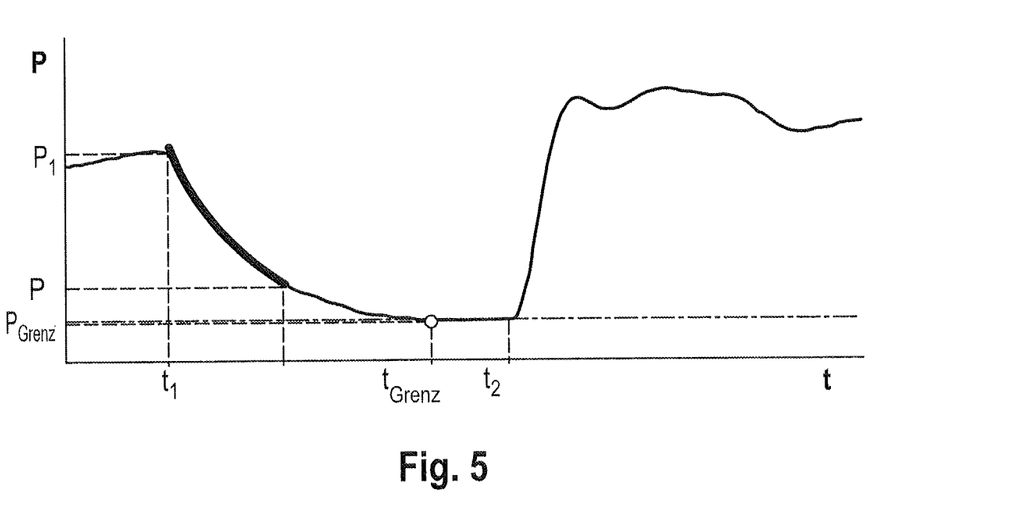
FIG. 5 shows an example of a pressure curve as well as of the time sequence of the method steps of an embodiment of the method according to aspects of the invention.

FIG. 5 shows an example of measurement in the case of proper needle connection. After closing the tube shut-off 40 the course of the venous pressure measured reaches a lower minimum pressure value ($p_{Grenz}$) measured. The threshold $P_{Grenz}$ reached or the pressure value calculated from an extrapolation and corresponding to said limit $p_{Grenz}$ can be used as a measure for the presence of needle dislodgement (see FIG. 7 in this context). The value τ describes the duration of the drop in the venous pressure measured from closing the tube shut-off 40 at the time $t_1$ to a $p_\tau$ of 36.8% of its value (1/e). This value τ, too, can be used as characteristic variable for determining needle dislodgement (see also FIG. 8 in this context).

Figure 6:
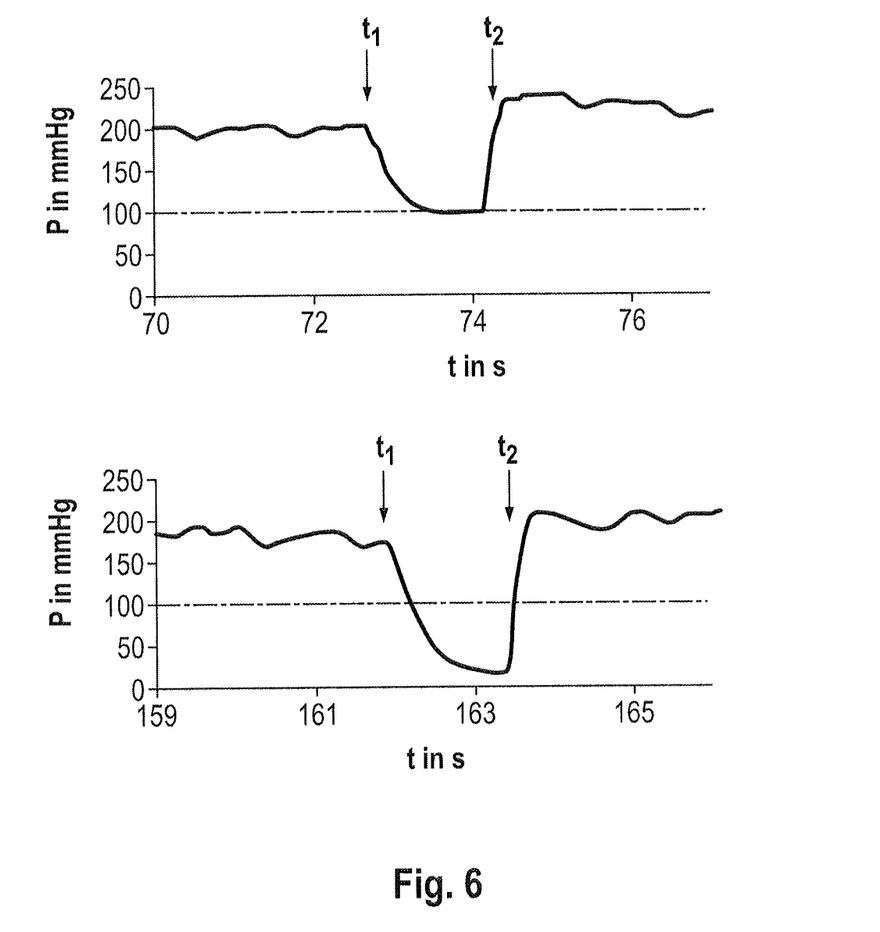
FIG. 6 shows in two series of curves pressure curves in time before, during and after a fluid flow shut-off.

FIG. 6 shows the different course of the blood pressure measured during the examination phase in the case of connection (upper curve) and dislodgement (lower curve). These two cases can be clearly separated from each other. In the case of dislodgement the measured pressure significantly falls below the value expected in the case of correct needle connection.

Figure 7:
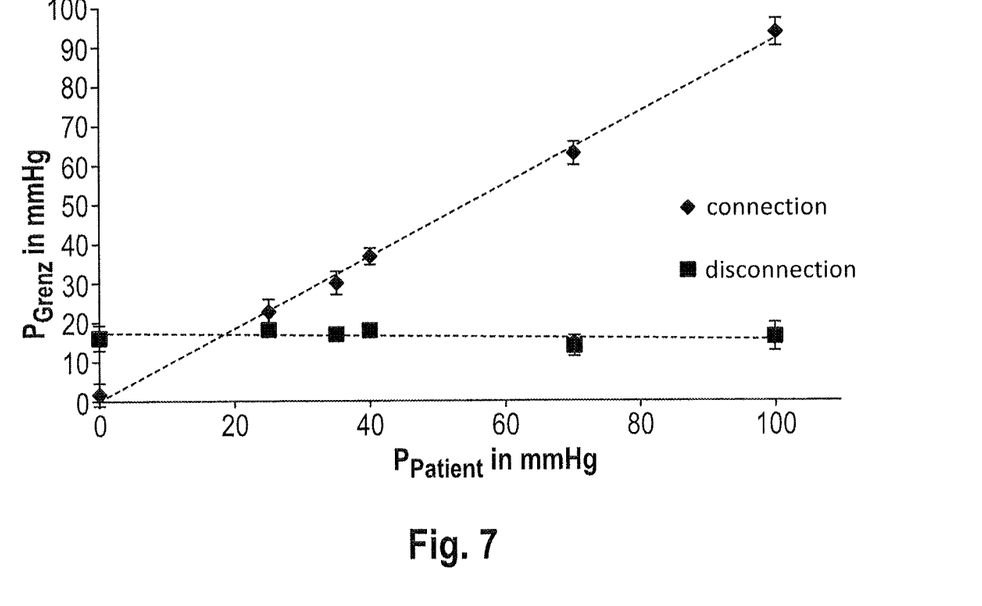
FIG. 7 illustrates two examples of the pressure curves in the case of proper needle connection or in the case of needle dislodgement.

FIG. 7 illustrates the difference between the limits or minimum values $p_{Grenz}$ in the case of connection and dislodgement. It is evident that in the range of low shunt or intravascular pressures ($p_{patient}$) no clear distinction can be made between connection and dislodgement. This fact is given, for example, when an extremely low shunt or intravascular pressure ($p_{patient}$) is prevailing and the venous needle after dislodgement experiences a negative change of height. This may occur, e.g., when the needle falls down from the edge of the table. In FIG. 7 the pressure values established in the case of connection including their limit of variation are applied by diamonds. The measuring values in the event of dislodgement are shown by lying squares.

Figure 8:
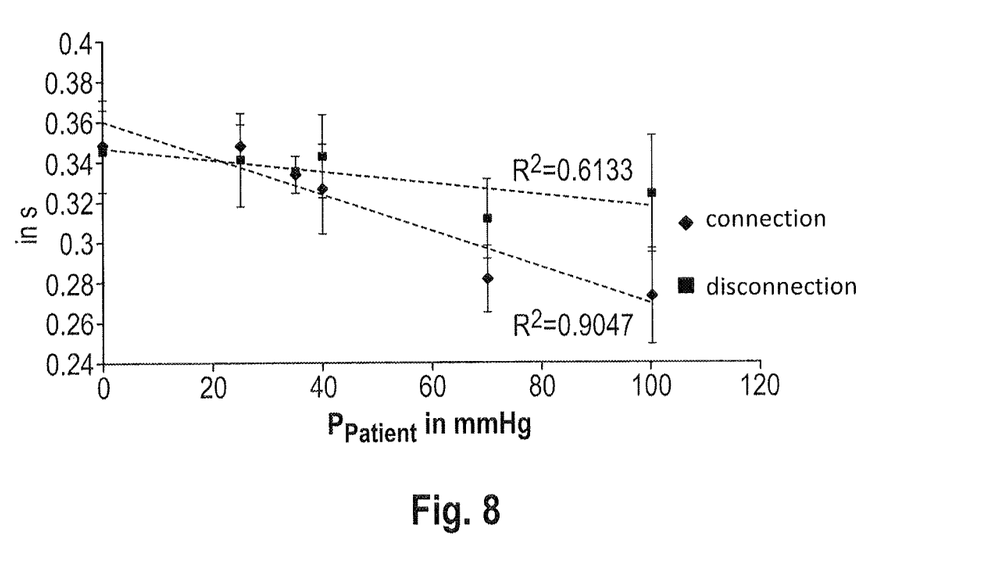
FIG. 8 shows two exemplary pressure curves in their time progression in the case of connection or dislodgement.

FIG. 8 shows the difference resulting in the cases of connection and dislodgement as regards the time parameter T. The case of dislodgement is illustrated here as linear approximation of the measuring values shown by lying squares. The case of connection, on the other hand, is symbolized as linear approximation of the diamonds. Upon evaluation the same statements are obtained as in the case of the evaluation according to FIG. 7. In the extreme case the value τ can be identical for connection and dislodgement.

The afore-described embodiments can be combined in any way, thereby separate further embodiments being provided. In addition, the method can also be implemented in the form of a computer program product in which codes for carrying out the individual method steps are included.

The invention claimed is:

1. An apparatus for detecting an interruption of connection between a blood treatment apparatus and a patient blood circulation which can be connected to the blood treatment apparatus, the apparatus comprising:
   a blood supply line of an extracorporeal blood circulation, wherein the blood supply line is connected upstream of the blood treatment apparatus for delivering blood from the patient blood circulation to the blood treatment apparatus;
   a blood discharge line of the extracorporeal blood circulation, wherein the blood discharge line is connected downstream of the blood treatment apparatus for returning blood from the blood treatment apparatus to the patient blood circulation;
   a valve or clamp arranged on the blood discharge line, the valve or clamp configured to selectively assume a closed position in which the valve or clamp blocks blood flow through the extracorporeal blood circulation at the valve or clamp;
   a pressure sensor configured to measure fluid pressure in the blood discharge line, the pressure sensor located at a position located between the valve or clamp and the patient blood circulation;
   a blood pump arranged on the extracorporeal blood circulation, wherein the blood pump continues to pump blood from the patient blood circulation while the valve or clamp is in the closed position;
   a collecting reservoir arranged on the extracorporeal blood circulation, wherein the collecting reservoir stores blood pumped from the blood pump while the valve or clamp is in the closed position; and
   a control and evaluation unit configured to evaluate the fluid pressure or a fluid pressure curve based on the measured fluid pressure occurring while the valve or clamp is in the closed position to detect an interruption or disturbance of the connection between the blood treatment apparatus and the patient blood circulation;
   wherein, while the valve or clamp is in the closed position, operation of the blood pump is terminated when the collecting reservoir is filled.

2. The apparatus of claim 1, wherein the apparatus is part of the blood treatment apparatus.

3. The apparatus of claim 1, wherein the blood treatment apparatus is a dialysis apparatus.

4. The apparatus of claim 1, further comprising at least one of a display or an alarm device for generating a display or an alarm, respectively, in the case of detection of an interruption or disturbance of the connection between the blood treatment apparatus and the patient blood circulation.

5. The apparatus of claim 1, wherein the control and evaluation unit is further configured to at least one of: compare the fluid pressure occurring in the blood discharge line after closing the valve or clamp to a threshold, determine a rate of pressure drop, determine a final fluid pressure value to be expected, or detect whether the measured fluid pressure tends toward atmospheric pressure or a higher pressure occurring in the patient blood circulation.

6. The apparatus of claim 1, wherein the collecting reservoir is a bubble collector.

7. The apparatus of claim 1, wherein the control and evaluation unit is further configured to stop the operation of a blood pump when at least one of an interruption or disturbance of the connection between the blood treatment apparatus and the patient blood circulation is determined, or a fluid pressure measured by the pressure sensor reaches or underruns a specific limit.

8. A method for detecting an interruption of a connection between a blood treatment apparatus and a patient blood circulation which can be connected to the blood treatment apparatus, the method comprising:
   pumping, with a blood pump arranged on an extracorporeal blood circulation, blood from the patient blood circulation;
   delivering, with a blood supply line of the extracorporeal blood circulation connected upstream of the blood treatment apparatus, blood from the patient blood circulation to the blood treatment apparatus;
   returning, with a blood discharge line of the extracorporeal blood circulation connected downstream of the blood treatment apparatus, blood to the patient blood circulation from the blood treatment apparatus;
   measuring fluid pressure prevailing in the blood discharge line at regular or irregular time intervals with a pressure sensor at a position located between a valve or clamp arranged on the blood discharge line and the patient blood circulation;
   blocking, with the valve or clamp, blood flow through the extracorporeal blood circulation at the valve or clamp at regular or irregular time intervals, wherein the blood pump continues pumping the blood from the patient blood circulation while the valve or clamp is blocking the blood flow through the extracorporeal blood circulation at the valve or clamp;
   storing, with a collecting reservoir arranged on the extracorporeal blood circulation, the blood pumped from the blood pump while the valve or clamp is blocking the blood flow through the extracorporeal blood circulation at the valve or clamp, wherein while the valve or clamp is blocking the blood flow through the extracorporeal blood circulation at the valve or clamp, operation of the blood pump is terminated when the collecting reservoir is filled; and
   evaluating, with a control and evaluation unit, the fluid pressure or a fluid pressure curve occurring in the extracorporeal blood circulation while the valve or clamp is blocking the blood flow through the extracorporeal blood circulation at the valve or clamp, so as to detect an interruption or disturbance of the connection between the blood treatment apparatus and the patient blood circulation.

9. The method according to claim 8, further comprising: generating at least one of a display or an alarm in the case of detection of interruption or disturbance of the connection between the blood treatment apparatus and the patient blood circulation.

10. The method according to claim 8, further comprising at least one of:
   comparing the measured fluid pressure occurring in the blood discharge line to a threshold while the valve or clamp is blocking the blood flow through the extracorporeal blood circulation at the valve or clamp,
   determining a rate of the pressure drop, or
   determining a final pressure value to be expected and detecting whether the final pressure value tends toward atmospheric pressure or a higher pressure occurring in the patient blood circulation.

11. The method according to claim 8, further comprising terminating operation of the blood pump when interruption or disturbance of the connection between the blood treatment apparatus and the patient blood circulation is determined.

12. The method according to claim 8, further comprising terminating operation of the blood pump when the fluid pressure measured by the pressure sensor reaches or underruns a specific limit.

13. The method according to claim 8, further comprising re-opening the valve or clamp as soon as no interruption or disturbance of the connection between the blood treatment apparatus and the patient blood circulation is detected as occurring.

14. The apparatus of claim 1, wherein the blood discharge line is connected to the patient blood circulation via a connector, and the interruption or disturbance of the connection between the blood treatment apparatus and the patient blood circulation is a dislodgement of the connector.

15. The apparatus of claim 14, wherein the connector is a venous needle.

16. The method according to claim 8, wherein the blood discharge line is connected to the patient blood circulation via a connector, and the interruption or disturbance of the connection between the blood treatment apparatus and the patient blood circulation is a dislodgement of the connector.

17. The method according to claim 16, wherein the connector is a venous needle.

* * * * *